United States Patent
Lambrecht et al.

(10) Patent No.: US 12,419,707 B2
(45) Date of Patent: Sep. 23, 2025

(54) GEARED ROLL DRIVE FOR MEDICAL INSTRUMENT

(71) Applicant: Intuitive Surgical Operations, Inc., Sunnyvale, CA (US)

(72) Inventors: Bram Gilbert Antoon Lambrecht, Redwood City, CA (US); Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 24 days.

(21) Appl. No.: 18/528,286

(22) Filed: Dec. 4, 2023

(65) Prior Publication Data

US 2024/0156551 A1 May 16, 2024

Related U.S. Application Data

(63) Continuation of application No. 17/223,723, filed on Apr. 6, 2021, now Pat. No. 11,864,851, which is a
(Continued)

(51) Int. Cl.
*A61B 34/30* (2016.01)
*A61B 17/00* (2006.01)
(Continued)

(52) U.S. Cl.
CPC ............. *A61B 34/30* (2016.02); *F16H 55/17* (2013.01); *A61B 2017/00477* (2013.01); *A61B 2034/302* (2016.02); *A61B 90/50* (2016.02)

(58) Field of Classification Search
CPC ... A61B 34/30; A61B 2034/302; A61B 90/50; A61B 2017/00477; F16H 55/17
See application file for complete search history.

(56) References Cited

U.S. PATENT DOCUMENTS

| 793,510 A | 6/1905 | Cramer et al. |
| 2,906,143 A | 9/1959 | Musser |

(Continued)

FOREIGN PATENT DOCUMENTS

| CN | 2573759 Y | 9/2003 |
| CN | 101893060 A | 11/2010 |

(Continued)

OTHER PUBLICATIONS

Final Office Action for U.S. Appl. No. 16/317,211, mailed Jan. 6, 2021.
(Continued)

*Primary Examiner* — Terence Boes

(57) ABSTRACT

A medical instrument includes a roll mechanism that rotates an instrument shaft. The roll mechanism may include a first gear coupled to the instrument shaft and meshed with a second gear. One of gears may be a spur gear while the other gear may be a beveloid gear. Further, the spur gear and the beveloid gear may be in a gear train containing a compressible gear, e.g., a gear with an inner center piece, an outer ring, and a flexible interconnecting structure between the inner center piece and the outer ring. With a compressible gear, an interference fit of in the gear train may be within manufacturing variations of the gear train, and the compressible gear may deflect radially away from the interference fit.

19 Claims, 7 Drawing Sheets

Related U.S. Application Data continuation of application No. 16/317,211, filed as application No. PCT/US2017/038805 on Jun. 22, 2017, now abandoned.

(60) Provisional application No. 62/362,340, filed on Jul. 14, 2016.

(51) Int. Cl.
*A61B 90/50* (2016.01)
*F16H 55/17* (2006.01)

(56) References Cited

U.S. PATENT DOCUMENTS

| | | |
|---|---|---|
| 4,899,608 A | 2/1990 | Knappe et al. |
| 5,207,691 A | 5/1993 | Nardella |
| 5,674,024 A | 10/1997 | Daumal et al. |
| 5,792,135 A | 8/1998 | Madhani et al. |
| 5,807,377 A | 9/1998 | Madhani et al. |
| 5,876,325 A | 3/1999 | Mizuno et al. |
| 6,007,550 A | 12/1999 | Wang et al. |
| 6,318,199 B1 | 11/2001 | Buck |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,817,974 B2 | 11/2004 | Cooper et al. |
| 6,994,708 B2 | 2/2006 | Manzo |
| 6,997,079 B2 | 2/2006 | Nomura et al. |
| 7,090,683 B2 | 8/2006 | Brock et al. |
| 7,169,141 B2 | 1/2007 | Brock et al. |
| 7,214,230 B2 | 5/2007 | Brock et al. |
| 7,331,967 B2 | 2/2008 | Lee et al. |
| 7,371,210 B2 | 5/2008 | Brock et al. |
| 7,524,320 B2 | 4/2009 | Tierney et al. |
| 7,608,083 B2 | 10/2009 | Lee et al. |
| 7,666,191 B2 | 2/2010 | Orban, III et al. |
| 7,752,937 B1 | 7/2010 | Dornan |
| 7,935,130 B2 | 5/2011 | Williams |
| 8,142,421 B2 | 3/2012 | Cooper et al. |
| 8,316,961 B2 | 11/2012 | Isobe et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,573,465 B2 | 11/2013 | Shelton, IV |
| 8,597,280 B2 | 12/2013 | Cooper et al. |
| 8,771,270 B2 | 7/2014 | Burbank |
| 8,800,838 B2 | 8/2014 | Shelton, IV |
| 8,992,565 B2 | 3/2015 | Brisson et al. |
| 9,002,518 B2 | 4/2015 | Manzo et al. |
| 9,028,494 B2 | 5/2015 | Shelton, IV et al. |
| 9,078,684 B2 | 7/2015 | Williams |
| 9,121,494 B2 | 9/2015 | Buchleitner et al. |
| 9,198,714 B2 | 12/2015 | Worrell et al. |
| 9,204,923 B2 | 12/2015 | Manzo et al. |
| 9,232,979 B2 | 1/2016 | Parihar et al. |
| 9,259,274 B2 | 2/2016 | Prisco |
| 9,259,275 B2 | 2/2016 | Burbank |
| 9,289,112 B2 | 3/2016 | Takemoto et al. |
| 9,572,616 B2 | 2/2017 | Vaughn |
| 9,664,262 B2 | 5/2017 | Donlon et al. |
| 9,737,373 B2 | 8/2017 | Schuh |
| 9,839,439 B2 | 12/2017 | Cooper et al. |
| 9,913,694 B2 | 3/2018 | Brisson |
| 9,931,106 B2 | 4/2018 | Au et al. |
| 9,993,313 B2 | 6/2018 | Schuh et al. |
| 10,016,244 B2 | 7/2018 | Cooper et al. |
| 10,022,193 B2 | 7/2018 | Cooper et al. |
| 10,076,348 B2 | 9/2018 | Anderson et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,314,583 B2 | 6/2019 | Smith et al. |
| 10,478,256 B2 | 11/2019 | Shelton, IV et al. |
| 10,543,051 B2 | 1/2020 | Schena et al. |
| 10,595,949 B2 | 3/2020 | Donlon et al. |
| 10,682,141 B2 | 6/2020 | Moore et al. |
| 10,806,530 B2 | 10/2020 | Liao et al. |
| 11,013,566 B2 | 5/2021 | Diel et al. |
| 11,076,926 B2 | 8/2021 | Ragosta et al. |
| 11,118,661 B2 | 9/2021 | Abbott |
| 11,304,770 B2 | 4/2022 | Crews et al. |
| 11,517,397 B2 | 12/2022 | Lambrecht et al. |
| 2002/0111635 A1 | 8/2002 | Jensen et al. |
| 2003/0068607 A1 | 4/2003 | Gregorio et al. |
| 2005/0042943 A1 | 2/2005 | Mocivnik et al. |
| 2005/0089345 A1 | 4/2005 | Yasumoto et al. |
| 2005/0119527 A1 | 6/2005 | Banik et al. |
| 2006/0276775 A1 | 12/2006 | Rosenberg et al. |
| 2007/0043338 A1 | 2/2007 | Moll et al. |
| 2007/0232858 A1 | 10/2007 | MacNamara et al. |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0087871 A1 | 4/2008 | Schena et al. |
| 2008/0103491 A1 | 5/2008 | Omori et al. |
| 2008/0196533 A1 | 8/2008 | Bergamasco et al. |
| 2009/0088774 A1 | 4/2009 | Swarup et al. |
| 2009/0110533 A1 | 4/2009 | Jinno et al. |
| 2009/0198272 A1 | 8/2009 | Kerver et al. |
| 2010/0011900 A1 | 1/2010 | Burbank et al. |
| 2010/0170519 A1 | 7/2010 | Romo et al. |
| 2010/0175701 A1 | 7/2010 | Reis et al. |
| 2010/0313706 A1 | 12/2010 | Hellinger et al. |
| 2010/0318101 A1 | 12/2010 | Choi et al. |
| 2011/0015650 A1 | 1/2011 | Choi et al. |
| 2011/0071543 A1 | 3/2011 | Prisco et al. |
| 2011/0118754 A1 | 5/2011 | Dachs, II et al. |
| 2011/0277775 A1 | 11/2011 | Holop et al. |
| 2011/0295269 A1 | 12/2011 | Swensgard et al. |
| 2011/0295270 A1 | 12/2011 | Giordano et al. |
| 2012/0046522 A1 | 2/2012 | Naito |
| 2012/0109186 A1 | 5/2012 | Parrott et al. |
| 2012/0123441 A1 | 5/2012 | Au et al. |
| 2012/0150192 A1 | 6/2012 | Dachs, II et al. |
| 2012/0239060 A1 | 9/2012 | Orban, III et al. |
| 2012/0289974 A1 | 11/2012 | Rogers et al. |
| 2012/0292367 A1 | 11/2012 | Morgan et al. |
| 2012/0298719 A1 | 11/2012 | Shelton, IV et al. |
| 2013/0046318 A1 | 2/2013 | Radgowski et al. |
| 2013/0123783 A1 | 5/2013 | Marczyk et al. |
| 2013/0144395 A1 | 6/2013 | Stefanchik et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0018821 A1 | 1/2014 | Yeung et al. |
| 2014/0100558 A1 | 4/2014 | Schmitz et al. |
| 2014/0107665 A1 | 4/2014 | Shellenberger et al. |
| 2014/0257333 A1 | 9/2014 | Blumenkranz |
| 2014/0276723 A1 | 9/2014 | Parihar et al. |
| 2015/0005786 A1 | 1/2015 | Burbank |
| 2015/0051034 A1 | 2/2015 | Cooper et al. |
| 2015/0150635 A1 | 6/2015 | Kilroy et al. |
| 2015/0157355 A1 | 6/2015 | Price et al. |
| 2016/0058443 A1 | 3/2016 | Yates et al. |
| 2016/0151115 A1 | 6/2016 | Karguth et al. |
| 2016/0157926 A1 | 6/2016 | Boudreaux |
| 2016/0184034 A1 | 6/2016 | Holop et al. |
| 2016/0184036 A1 | 6/2016 | Solomon et al. |
| 2016/0184037 A1 | 6/2016 | Cooper et al. |
| 2016/0199138 A1 | 7/2016 | Cooper et al. |
| 2016/0296219 A1 | 10/2016 | Srivastava et al. |
| 2016/0338762 A1 | 11/2016 | Krastins et al. |
| 2016/0361049 A1 | 12/2016 | Dachs, II et al. |
| 2017/0007345 A1 | 1/2017 | Smith et al. |
| 2017/0027656 A1 | 2/2017 | Robert et al. |
| 2017/0165017 A1 | 6/2017 | Chaplin et al. |
| 2017/0172672 A1 | 6/2017 | Bailey et al. |
| 2017/0207467 A1 | 7/2017 | Shelton, IV et al. |
| 2017/0248194 A1* | 8/2017 | Bae .............. F16H 57/023 |
| 2018/0055583 A1 | 3/2018 | Schuh et al. |
| 2018/0126504 A1 | 5/2018 | Shelton, IV et al. |
| 2018/0214223 A1 | 8/2018 | Turner |
| 2018/0229021 A1 | 8/2018 | Donlon et al. |

(56) References Cited

U.S. PATENT DOCUMENTS

| | | |
|---|---|---|
| 2018/0243036 A1 | 8/2018 | Donlon et al. |
| 2019/0038282 A1 | 2/2019 | Shelton, IV et al. |
| 2019/0099227 A1 | 4/2019 | Rockrohr |
| 2019/0117325 A1 | 4/2019 | Kishi |
| 2019/0125468 A1 | 5/2019 | Adams |
| 2019/0192137 A1 | 6/2019 | Shelton, IV et al. |
| 2019/0231451 A1 | 8/2019 | Lambrecht et al. |
| 2019/0231464 A1 | 8/2019 | Wixey et al. |
| 2019/0239965 A1 | 8/2019 | Abbott |
| 2019/0298323 A1 | 10/2019 | Lambrecht et al. |
| 2019/0307522 A1 | 10/2019 | Lambrecht et al. |
| 2019/0328467 A1 | 10/2019 | Waterbury et al. |
| 2020/0138473 A1 | 5/2020 | Shelton, IV et al. |
| 2020/0197117 A1 | 6/2020 | Donlon et al. |
| 2021/0093408 A1 | 4/2021 | Carey et al. |
| 2021/0220062 A1 | 7/2021 | Lambrecht et al. |
| 2021/0322118 A1 | 10/2021 | Donlon et al. |
| 2021/0401523 A1 | 12/2021 | Suresh et al. |
| 2021/0401524 A1 | 12/2021 | Suresh et al. |
| 2022/0000572 A1 | 1/2022 | Ragosta et al. |
| 2022/0192764 A1 | 6/2022 | Waterbury et al. |
| 2023/0172680 A1 | 6/2023 | Reid et al. |
| 2024/0100942 A1* | 3/2024 | Mattsson .............. F16H 37/082 |
| 2024/0197423 A1 | 6/2024 | Ragosta et al. |
| 2024/0315792 A1 | 9/2024 | Lambrecht et al. |
| 2024/0366329 A1 | 11/2024 | Kadokura |
| 2024/0382279 A1 | 11/2024 | Baldwin et al. |
| 2025/0000598 A1 | 1/2025 | Baldwin et al. |

FOREIGN PATENT DOCUMENTS

| | | |
|---|---|---|
| CN | 109505951 A | 3/2019 |
| CN | 110269686 A | 9/2019 |
| EP | 3103374 A1 | 12/2016 |
| JP | H06114000 A | 4/1994 |
| JP | H10249777 A | 9/1998 |
| JP | 2003024336 A | 1/2003 |
| JP | 2005288590 A | 10/2005 |
| WO | WO-9729690 A1 | 8/1997 |
| WO | WO-0030557 A1 | 6/2000 |
| WO | WO-2009039506 A1 | 3/2009 |
| WO | WO-2010009224 A1 | 1/2010 |
| WO | WO-2011060046 A2 | 5/2011 |
| WO | WO-2012068156 A2 | 5/2012 |
| WO | WO-2012166806 A1 | 12/2012 |
| WO | WO-2015142290 A1 | 9/2015 |
| WO | WO-2016073637 A1 | 5/2016 |
| WO | WO-2016161449 A1 | 10/2016 |
| WO | WO-2016172299 A1 | 10/2016 |
| WO | WO-2017188851 A1 | 11/2017 |
| WO | WO-2018013313 A1 | 1/2018 |
| WO | WO-2018049217 A1 | 3/2018 |
| WO | WO-2018094191 A1 | 5/2018 |

OTHER PUBLICATIONS

International Search Report and Written Opinion for Application No. PCT/US2017/038805, mailed on Oct. 30, 2017, 13 pages.

Litvin F.L., et al., "Face Gear Drive with Helical Involute Pinion: Geometry, Generation by a Shaper and a Worm, Avoidance of Singularities and Stress Analysis," NASA/CR-2005-213443, ARL-CR-557, Feb. 2005, 62 pages.

Litvin F.L., et al., "Handbook on Face Gear Drives with a Spur Involute Pinion," NASA/CR-2000-209909, ARL-CR-447, Mar. 2000, 106 pages.

Non-Final Office Action mailed Jul. 23, 2020 for U.S. Appl. No. 16/317,211 filed Jan. 11, 2019.

Office Action for CN Application No. 201910292780.4, mailed Jan. 28, 2021.

Office Action for U.S. Appl. No. 17/223,723, mailed May 23, 2023, 08 pages.

Smith L.J., "The Involute Helicoid and the Universal Gear," Gear Technology, Nov./Dec. 1990, pp. 18-27.

Stadtfeld H, Dr., "Tribology Aspects in Angular Transmission Systems: Part I—General Explanations on Theoretical Bevel Gear Analysis," Gear Technology, Aug. 2010, URL: https://www.geartechnology.com/issues/0810x/stadtfeld1.pdf , pp. 46-52.

Stadtfeld H, Dr., "Tribology Aspects in Angular Transmission Systems: Part II—Straight Bevel Gears," Gear Technology, Sep.-Oct. 2010, URL: http://www.geartechnology.com/issues/0910x/stadtfeld.pdf , pp. 47-52.

Stadtfeld H. Dr., "Tribology Aspects in Angular Transmission Systems: Part III—Zerol Bevel Gears," Gear Technology, Nov.-Dec. 2010, URL: http://www.geartechnology.com/issues/1110x/zerol.pdf , pp. 42-47.

Stadtfeld H, Dr., "Tribology Aspects in Angular Transmission Systems: Part IV—Spiral Bevel Gears," Gear Technology, Jan.-Feb. 2011, URL: https://www.geartechnology.com/issues/0111x/stadtfeld.pdf , pp. 66-72.

Stadtfeld H. Dr., "Tribology Aspects in Angular Transmission Systems: Part V—Face Gears," Gear Technology, Mar.-Apr. 2011, URL: http://www.geartechnology.com/issues/0311x/stadtfeld.pdf , pp. 47-52.

Stadtfeld H, Dr., "Tribology Aspects in Angular Transmission Systems: Part VI—Beveloid & Hypoloid Gears," Gear Technology, May 2011, URL: https://www.geartechnology.com/issues/0511x/beveloid.pdf , pp. 48-52.

Stadtfeld H, Dr., "Tribology Aspects in Angular Transmission Systems: Part VII—Hypoid Gears," Gear Technology, Jun.-Jul. 2011, URL: https://www.geartechnology.com/issues/0611x/hypoid.pdf , pp. 66-72.

Stadtfeld H, Dr., "Tribology Aspects in Angular Transmission Systems: Part VIII—Super-Reduction Hypoid Gears," Gear Technology, Aug. 2011, URL: http://www.geartechnology.com/issues/0811x/superhypoid.pdf , pp. 42-48.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

GEARED ROLL DRIVE FOR MEDICAL INSTRUMENT

RELATED APPLICATION

This patent application is a continuation of U.S. application Ser. No. 17/223,723 (filed Apr. 6, 2021), entitled "GEARED ROLL DRIVE FOR MEDICAL INSTRUMENT," which is a continuation of U.S. application Ser. No. 16/317,211 (filed Jan. 11, 2019), entitled "GEARED ROLL DRIVE FOR MEDICAL INSTRUMENT," which is a U.S. national stage filing under 35 U.S.C. § 371 of International Application No. PCT/US2017/038805 (filed Jun. 22, 2017), entitled "GEARED ROLL DRIVE FOR MEDICAL INSTRUMENT," which claims priority to and the filing date benefit of U.S. Provisional Patent Application No. 62/362,340 (filed Jul. 14, 2016), entitled "GEARED ROLL DRIVE FOR MEDICAL INSTRUMENT," each of which is incorporated by reference herein in its entirety.

BACKGROUND

Minimally-invasive medical procedures often employ medical instruments having a tool or manipulator apparatus (often called an "end effector") at the distal end of an elongated instrument shaft. During a minimally-invasive medical procedure, the distal ends of one or more medical instruments may be inserted through one or more small incisions and/or natural lumens in order to position the tools at a work site in a patient. A surgeon or other user may then control the tools to perform desired clinical functions at the work site, e.g., endoscopy, laparoscopy, arthroscopy, hypodermic injection, air-pressure injection, subdermal implants, refractive surgery, percutaneous surgery, cryosurgery, microsurgery, keyhole surgery, endovascular surgery such as angioplasty, coronary catheterization, placement of internal electrodes, and stereotactic surgery.

The manipulations required or desired to effectively complete medical procedures can be complex and intricate. Accordingly, medical instruments for minimally-invasive medical procedures may need to provide precise control of many mechanical degrees of freedom of movement. For example, a user performing a procedure may need to position and orient a distal tool to target the distal tool on specific tissue and the tool must be able to maneuver at the work site to achieve the desired position and orientation. The user may then need to move the distal tip of the tool to interact with the target tissue and perform a clinical function of the tool, e.g., clamping, cutting, or cauterizing of the target tissue. Some of the of the degrees of freedom required for such manipulations may include: translation of distal tip of the instrument shaft in an insertion direction; actuation of one or more joints located along the instrument shaft or in the tool; rotation of the instrument shaft about a length axis of the instrument shaft; and opening and closing of a grip or scissors feature of the distal tool. Since directly controlling multiple degrees of freedom may be difficult for a human operator, some advanced medical systems employ a robot to aid in the control of the degrees of freedom of medical instruments and thereby provide the user with a more intuitive operation. (As used herein, the terms "robot" or "robotically" and the like include teleoperation or non-teleoperation aspects, as well as telerobotic and non-telerobotic aspects.) Medical instruments that provide all of the degrees of freedom required or desired for medical procedures and that are suitable for use with robotic systems are often complex and difficult to assemble.

SUMMARY

In accordance with an aspect of the invention, a medical instrument may include a roll mechanism that rotates an instrument shaft, and the roll mechanism may include a spur gear and a beveloid gear to accommodate an angle between the instrument shaft and a rotation axis of an input spindle. The spur gear and the beveloid gear may further be in a gear train containing a compressible gear. With a compressible gear, an interference fit of in the gear train may be within manufacturing variations of the gear train because the compressible gear is able to deflect radially away from the interference.

One specific implementation is a medical instrument that includes an instrument shaft and a roll mechanism coupled to rotate of the instrument shaft. The roll mechanism may particularly include a first gear coupled to the instrument shaft and a second gear meshed with the first gear. One of the first gear and the second gear is a beveloid gear, and the other of the first and second gears may be a spur gear, a helical cylindrical gear, or another beveloid gear.

Another specific implementation is a mechanism including a compressible gear. The compressible gear may particularly include a center inner piece, an outer ring, and an interconnecting member that connects the inner piece to the outer ring and allows the outer ring to radially compress inward toward the center in response forces that result from interactions with adjacent gears.

DETAILED DESCRIPTION

Figure 1:
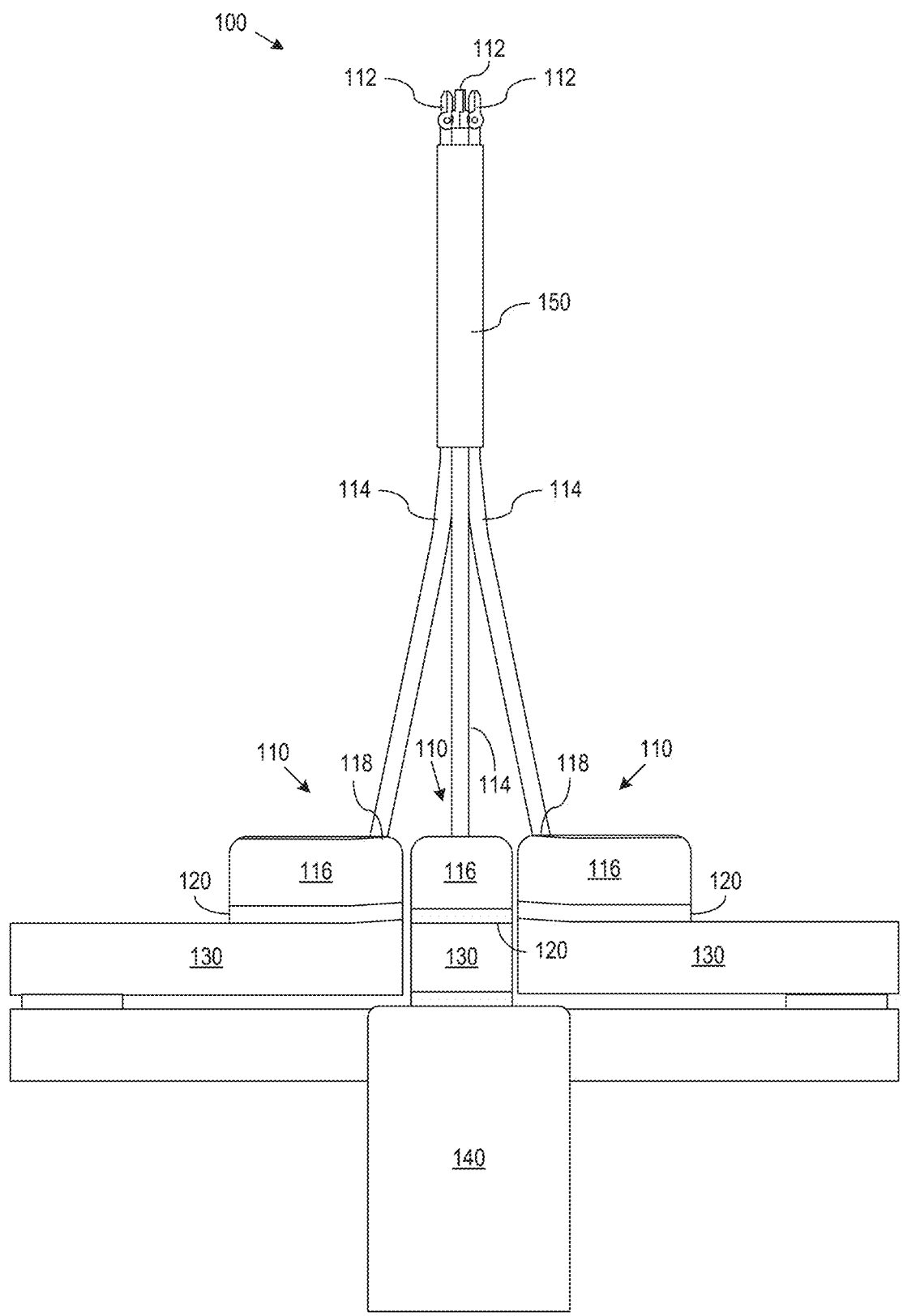
FIG. 1 illustrates a single-port robotic medical system that can deploy the distal tools of multiple instruments to simultaneously work in close proximity.

A single-port medical system instruments may deploy the shafts of multiple medical instruments through a single port, e.g., an incision, so that tools at the distal ends of the instrument shafts can work close to each other. FIG. 1, for example, shows a medical system 100 in which multiple medical instruments 110 are respectively mounted on docking ports 120 on arms 130 of a robot 140. Each medical instrument 110 has a backend ("proximal") mechanism 116 with a housing having a tapered nose 118 from which an instrument shaft 114 extends. In the illustrated configuration, noses 118 of instruments 110 may be wedge shaped, so multiple instruments 110, e.g., four instruments 110, may be arranged like pie pieces in a compact configuration that positions instrument shafts 114 close to each other. Each instrument shaft 114 exits the corresponding backend mechanism 116 at an angle (e.g., about 5°) from perpendicular to the docking surface of the backend mechanism 116, so that instrument shafts 114 converge and can be elastically bent for insertion through one or more cannulas 150 that guide portions of all of the instrument shafts 114 close to a port axis (e.g., an axis extending distally from the center of the pie configuration of backend mechanisms 116 to the port).

Figure 2A:
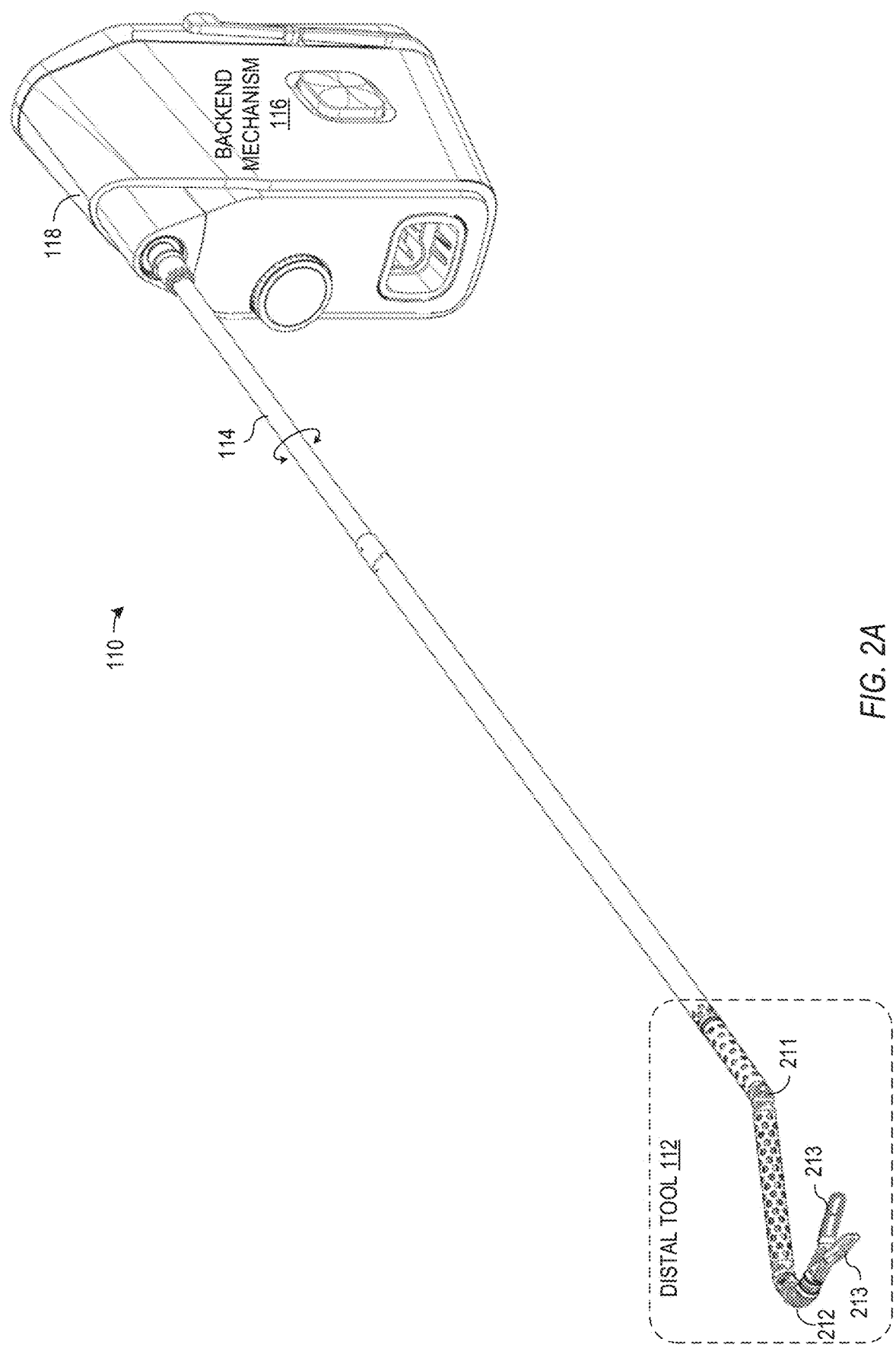
FIGS. 2A and 2B show perspective and top views of an example implementation of a medical instrument.
Figure 2B:
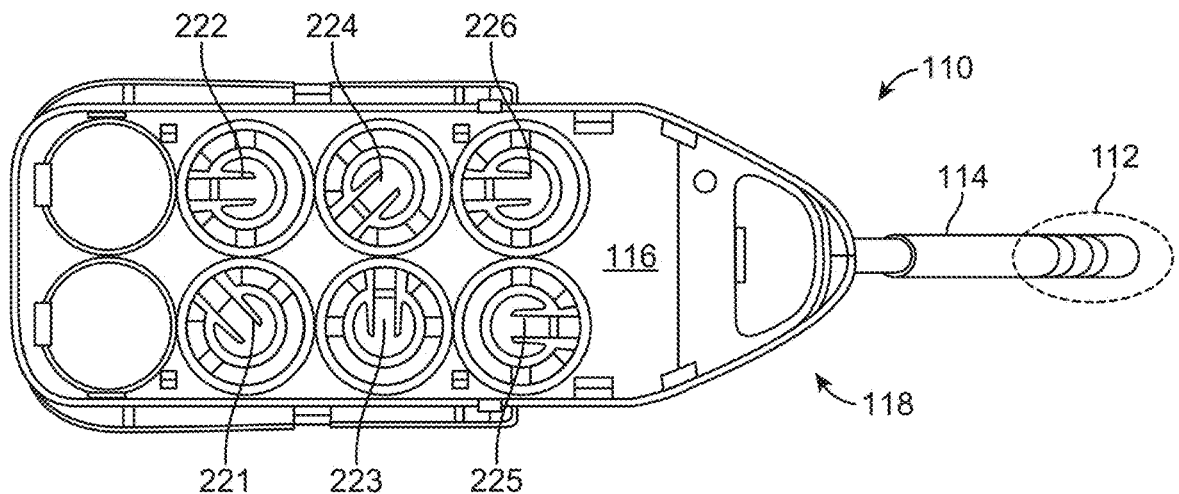

FIGS. 2A and 2B illustrate perspective and top views of an example implementation of a medical instrument 110 suitable for use in medical system 100 of FIG. 1. As shown, the illustrated implementation of medical instrument 110 includes a tool 112 at the distal end of an instrument shaft 114 that extends from near nose 118 of backend mechanism 116. Distal tool 112 and instrument shaft 114 may have multiple degrees of freedom of movement relative to backend mechanism 116. In the illustrated configuration of FIG. 2A, medical instrument 110 has six degrees of freedom corresponding to: two types of actuation of a first wrist or joint 211; two more types of actuation of a second wrist or joint 212; opening or closing movement of jaws 213; and rotations of instrument shaft 114 about its central or length axis. Other implementations of medical instruments may provide more, fewer, or different degrees of freedom of movement.

Backend mechanism 116 as shown in FIG. 2B has six input spindles 221 to 226 with exterior engagement features that are shaped and positioned to engage actuators (e.g., drive motors) in a docking port of a robot (e.g., docking ports 120 of robot 140 shown in FIG. 1). In this specific example, first and second actuators in the robot can rotate input spindles 221 and 222 to control actuation of wrist or joint 211. Third and fourth actuators in the robot can rotate input spindles 223 and 224 to control actuation of wrist or joint 212. A fifth actuator may rotate input spindle 225 to control opening or closing 205 of jaws 213, and a sixth actuator may rotate input spindle 226 to control roll rotation of instrument shaft 114. In accordance with one aspect disclosed herein, backend mechanism 116 includes a roll mechanism that may act as a transmission to convert the rotation of input spindle 226 into roll rotation of instrument shaft 114.

Tapering of the housing of backend mechanism 116 at nose 118 allows a compact arrangement of instruments as described above but also limits the available space in nose 118 for input spindles. Input spindle 226, which controls roll rotations of shaft 114, is accordingly offset from the location from which instrument shaft 114 exits backend mechanism 116. For this configuration, backend mechanism 116 needs a roll mechanism to transmit rotation of input spindle 226 across a distance to cause rotation of instrument shaft 114. The roll mechanism needs to fit into the tapered space available at nose 118 of backend mechanism 116, needs to exhibit low backlash for precise control of the angular position of instrument shaft 114, and needs to accommodate the difference in the orientations or input spindle 226 and instrument shaft 114, e.g., the angle between the rotation axis of input spindle 226 and the rotation axis of instrument shaft 114. The roll mechanism also would ideally be easy to manufacture and assemble.

Figure 3A:
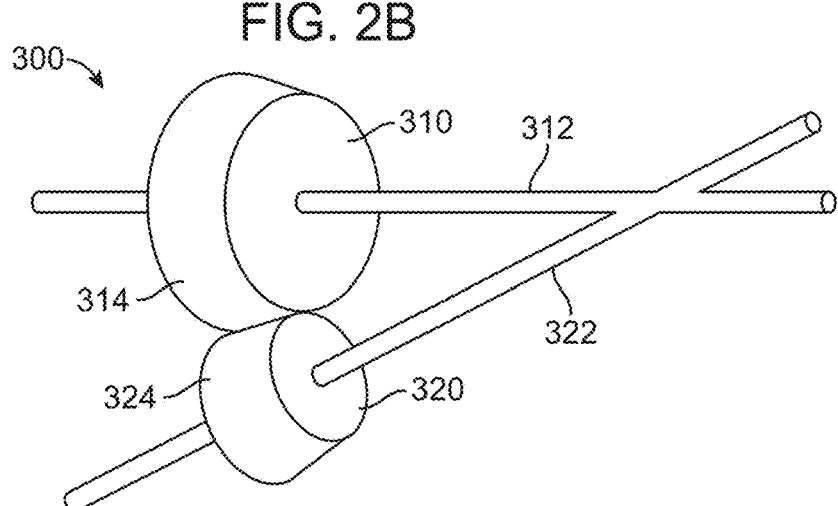
FIG. 3A illustrates use of bevel gears to transfer rotation about input axis to rotation about an output axis that is at an angle with the input axis.

One method for transferring rotation and accommodating an angle between rotation axes employs bevel gears. FIG. 3A, for example, shows a system including a bevel gear system 300 including bevel gears 310 and 320. In general, bevel gears are gears that have conically-shaped tooth-bearing faces and are arranged so rotation axes of the gears intersect. FIG. 3A shows bevel gears 310 and 320 having intersecting shafts or rotation axes 312 and 322. For ease of illustration, FIG. 3A does not show tooth patterns on tooth-bearing faces 314 and 324 (also called tooth-bearing surfaces 314, 324) of gears 310 and 320, but a variety of different patterns (e.g., straight, spiral, or zerol tooth lines) could be employed in different implementations. Bevel gears can accommodate the angle between rotation axes 312 and 322 when axes 312 and 322 intersect, but changes in axial position of bevel gear 310 or 320 may change backlash, i.e., change the clearance between mated teeth on surfaces 314 and 324. In particular, a line of contact between tooth-bearing surfaces 314 and 324 is generally not parallel to either rotation axis 312 or 322, so that movement of gear 310 or 320 along axis 312 or 322 changes the clearance of the gear teeth and may cause clash or increased play when teeth mesh.

Each bevel gear 310 or 320 is generated from a conical surface. FIG. 3C, for example, illustrates a relationship of a single tooth 316 on a conical surface 318. Bevel gear 310 normally includes multiple teeth identical to tooth 316 and the teeth are uniformly distributed around conical surface 318. FIG. 3C shows an area 316' in which a tooth adjacent to tooth 316 would reside. The boundaries of each such tooth 316, if sufficiently extended, converge to the apex of conical surface 318. Accordingly, each cross-section of gear 310 or 320 perpendicular to its rotation axis may have substantially the same shape, but that shape is scaled in size according to the radius of the addendum circle. In particular, teeth in all cross sections of gear 310 or 320 have the same angular dimensions. Additionally, bevel gears 310 and 320, being conjugate gears, generally must have the same diametrical pitch at their back cones, must be mated flush, must have complementary cone angles equal to the sum of the shaft angle, and must have a common apex.

Figure 3B:
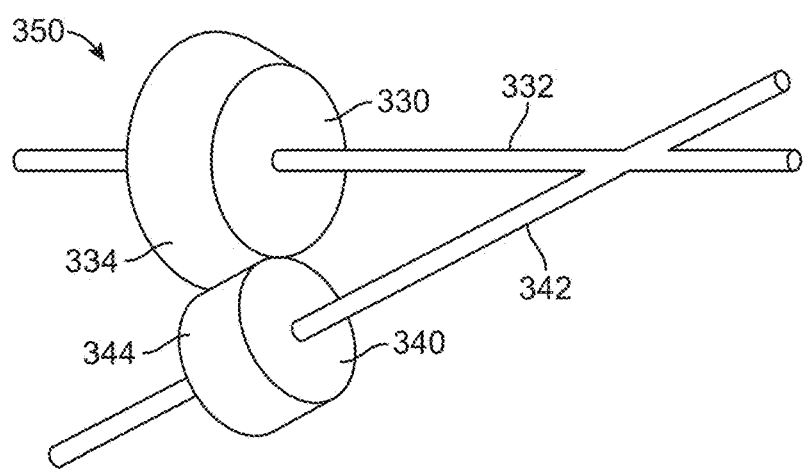
FIG. 3B illustrates use of a beveloid or taper gear to transfer rotation about input axis to rotation about an output axis that is at an angle with the input axis.
Figure 3C:
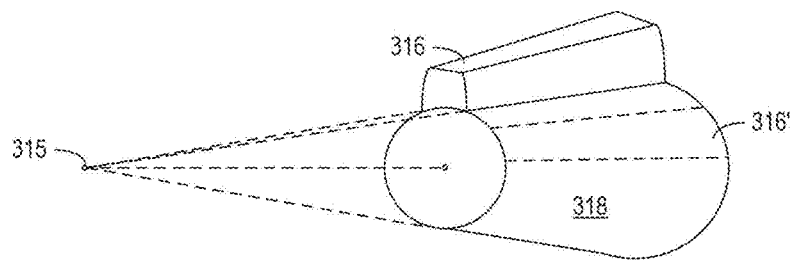
FIG. 3C illustrates a tooth on a bevel gear.

FIG. 3B shows a beveloid or taper gear system 350 that accommodates an angle between a shaft or rotation axis 332 of an input gear 330 and a shaft or rotation axis 342 of an output gear 340. In FIG. 3B, input gear 330 is a taper gear having a conically-shaped tooth bearing face 334, and output gear 340 may be a spur gear, a helical cylindrical gear, or another taper gear having a tooth bearing face 344. A beveloid gear has a pressure angle that changes from the toe to the heel of the gear so that the nominal center distance to the spur gear changes according to the distance along the angled axes. In configuration of FIG. 3B, for example, teeth on face 334 of input gear 330 may have a small addendum shift, and therefore a smaller effective pressure angle, toward the narrower side of input gear 330, and a large addendum shift, and therefore a larger effective pressure angle, toward the larger side of input gear 330 so that output gear 340 may have uniformly sized and shaped teeth and still properly mesh with input gear 330. With this configuration, when surface 344 is cylindrical, a change in the axial position of gear 340 does not change the backlash between gears 330 and 340, which makes beveloid gear system 350 of FIG. 3B more tolerant of axial misalignment or changes in alignment that could arise during assembly or use of a medical instrument. This is in contrast to the "flush mating" of the back cones required for bevel gears.

Figure 3D:
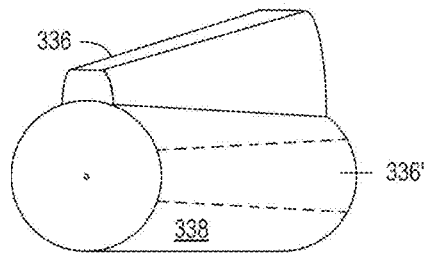
FIG. 3D illustrates a tooth on a beveloid or taper gear.

Beveloid or taper gear 330, in contrast to bevel gears 310 and 320, has a tooth pattern generated from a cylindrical surface. FIG. 3D, for example, shows a single tooth 336 on a cylindrical surface 338. A complete gear 330 may include multiple identical teeth 336 arranged uniformly around cylindrical surface 338, and an area 336' marks a location where a tooth adjacent to tooth 336 may reside. All straight line vertices of each tooth 336 on the beveloid gear of FIG. 3D converge not to the same point but points on a circle and in a common plane. Angular symmetry is not preserved along a tooth 336 of a beveloid gear, and in each cross-section, tooth 336 has a different angular size with the angular size decreasing with the radius of the addendum circle of the gear, and the adjacent tooth space between teeth correspondingly increases to accommodate a tooth of a spur gear, e.g., gear 340.

Figure 3E:
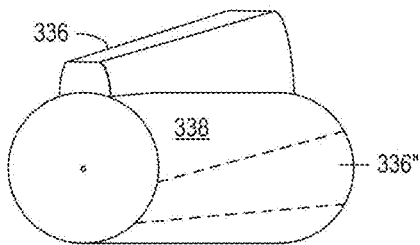
FIG. 3E illustrates a tooth on a beveloid or taper gear with a non-zero helix angle.

FIG. 3E illustrates how a beveloid gear may have teeth with a helix angle. In particular, tooth areas such as area 336" on cylindrical surface 338 may be at an angle to the shaft of the beveloid gear. A beveloid gear system such as system 350 of FIG. 3B may employ a beveloid gear 330 with a helix angle such as illustrated in FIG. 3E to provide a skew between rotation axes 332 and 342, i.e., so that rotation axes 332 and 342 do not intersect. Alternatively or additionally, a helix angle on output gear can provide or adjust a skew between axes 332 and 342.

Gear 340 of FIG. 3B may have teeth shaped to mate with a range of different diametral pitch found on beveloid gear 330. (The diametral pitch may be defined as the ratio of the number of teeth and the diameter of a gear.) In particular, a known mathematical relationship between the diametral pitch and the pressure angle (i.e., the angle of the tooth face) can be used to determine a tooth shape that allows gear 340 to mate with a range of different diametral pitches such as found on a particular beveloid or taper gear 330. As described above, the range of diametral pitch on a beveloid gear depends on angle between axes 332 and 342, because the number of teeth remains constant, and the diameter of gear 330 changes at a rate that depends on the angle between axes 332 and 342. Compensating for the larger diametral pitch with a smaller pressure angle allows gear 340 to continue to mesh with taper gear 330.

FIG. 3B shows a beveloid gear system 350 in which input and output rotation axes 332 and 342 intersect. Alternatively, input axis 332 and output axis 342 may not lie in the same plane, i.e., axes 332 and 342 may be skewed. To accommodate skew, the teeth of gear 330 may further have a small helix angle (e.g., less than about 2°) to create an asymmetric tooth which compensates for the small change in the way the teeth mesh up with gear 340 if axes 332 and 342 are skewed instead of intersecting. The helix angle may be desired to create a skew between input and output axes of a gear train, for example, when an input spindle 226 is not in the center of instrument 110 of FIG. 2A but instrument shaft 114 is centered and at an angle to the input spindle 226.

Figure 4A:
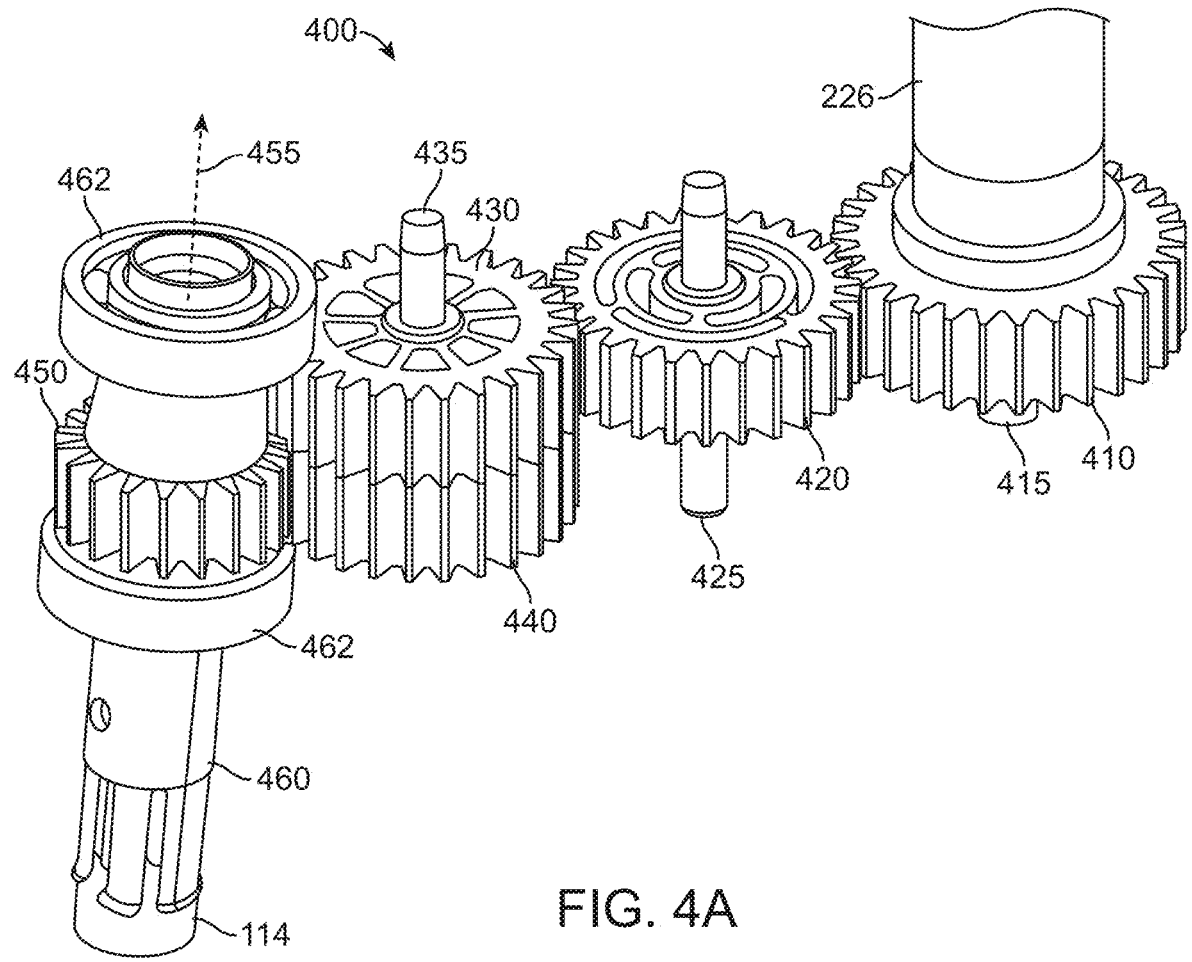
FIG. 4A shows one implementation of a roll mechanism using a beveloid or taper gear and idler gears to convert rotation of input spindle to rotation into rotation of an instrument shaft.
Figure 4B:
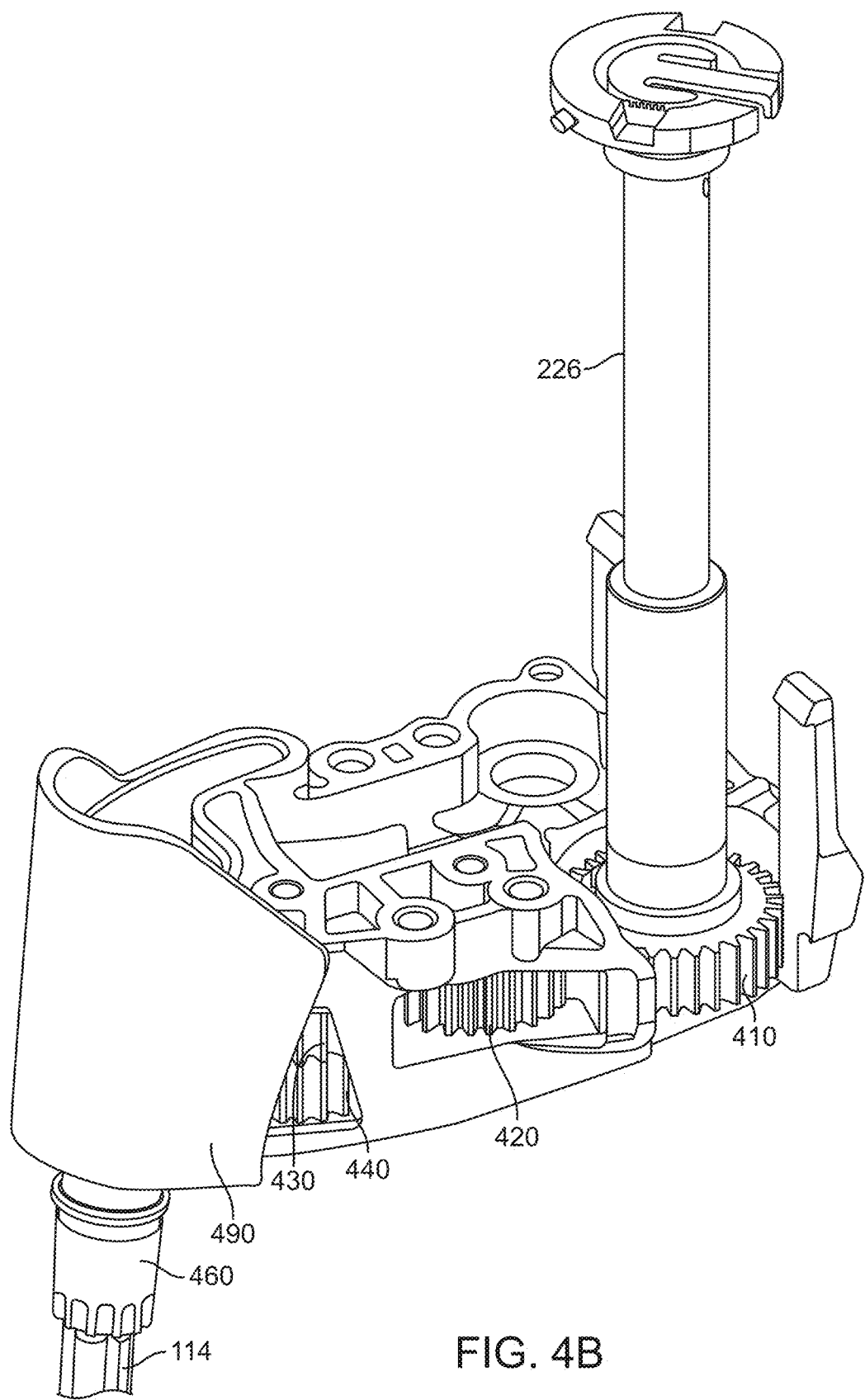
FIG. 4B shows an implementation of a roll mechanism assembled in a portion of a chassis of a medical instrument.

FIG. 4A shows a roll mechanism 400 for a medical instrument, which employs a beveloid gear system. Roll mechanism 400 particularly includes an input gear 410, which may be affixed to an input spindle 226 of a medical instrument such as described above. Input gear 410 meshes with an idler gear 420, which meshes with a spur gear 430. Spur gear 430 is affixed to a beveloid gear 440 so that gears 430 and 440 rotate together about a common shaft 435. Beveloid gear 440 in turn meshes with an output gear 450 that attaches to an instrument shaft 114. (Gears 430 and 440 may be formed together as a single monolithic piece although functionally described here as two gears because of interactions with adjacent gears in a gear train.) In the illustrated implementation, output gear 450 attaches to a mounting 460 into which instrument shaft 114 can be inserted or attached, and mounting 460 may include bearings 462 capable of supporting a long instrument shaft. FIG. 4B illustrates how roll mechanism 400 may be assembled or mounted in a piece 490 of a chassis of a backend mechanism. In other embodiments, zero or two or more idler gears may be included in the roll mechanism.

Gears 410, 420, 430, and 440 may be aligned so that shafts 415, 425, and 435 of gears 410, 420, and 430 are parallel and lie in the same plane, which may allow smooth operation mechanism 400 by avoiding interference or backlash. In an exemplary embodiment, shaft 455 of gear 450 is at an angle of about 5° with input shaft 415 of gear 410 and input spindle 226, and gear 450 and beveloid gear 440 may have a helical tooth pattern, so that shaft 455 is not in the same plane as shafts 415, 425, and 435. The center of gear 450 may, however, be in the plane of shafts 415, 425, and 435 to closely approximate a gear train having all rotation shafts parallel and coplanar. In general, backlash can be reduced when a gear train has gears with co-planar shafts when compared to a gear train in which the shaft of one or more gears is offset from a plane containing the shafts of other gears.

Figure 5A:
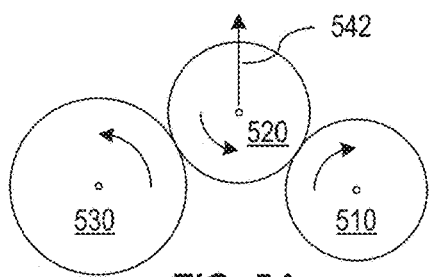
FIGS. 5A and 5B illustrate reaction forces on an idler gear for different rotation directions of gear train in which the shaft of the idler is not in the same plane as the shafts of input and output gears.
Figure 5B:
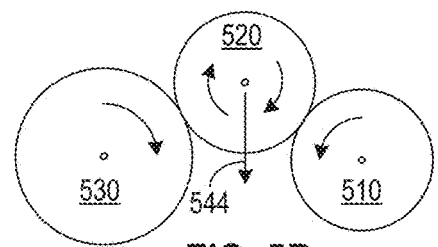
Figure 5C:
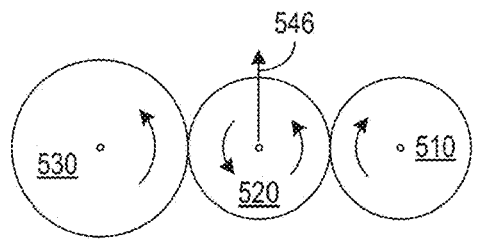
FIG. 5C illustrates the reaction force on an idler gear when axes of input, idler, and output gears are aligned in the same plane.

FIGS. 5A and 5B illustrate a gear train in which an idler gear 520 has a shaft that is offset from a plane containing the shaft of an input gear 510 and the shaft of an output gear 530. In the configuration of FIG. 5A, when input gear 510 rotates clockwise, a reaction force 542 on idler gear 520 results from the action of the teeth of input gear 510 to turn idler gear 520 and the action of the teeth of idler gear 520 to turn output gear 530, and reaction force 542 tends to push idler gear 520 away from gears 510 and 520. In contrast, when input gear 510 rotates counterclockwise as shown in FIG. 5B, a reaction force 544 that results from the action of the teeth of input gear 510 to turn idler 520 and the action of the teeth of idler gear 520 to turn output gear 530 tends to pull idler gear 520 between from gears 510 and 520, which may result in gear interference or binding. Even when interference does not occur, the change in reaction forces 542 or 544 when the rotation direction of input gear 510 changes can change backlash. In contrast, when input, idler, and output gears 510, 520, and 530 are aligned along a straight line as shown in FIG. 5C, the reaction force 546 resulting from either direction of rotation of input gear 510 does not tend to change the separation of gears 510, 520, and 530.

The shafts of interacting gears, such as in mechanism 400 of FIG. 4A, are generally spaced to provide clearance between the teeth of the interacting gears. The clearance allows for small variations in the shapes of the teeth, in run-out of the gear teeth relative to the shaft, and in the locations of the bearings or shaft centers. However, the clearance also results in backlash when the gears change rotation directions. Each additional gear mesh in the gear train adds backlash to the overall system. To minimize backlash, the gear teeth and shaft spacing may be tightly toleranced, but some manufacturing techniques may have difficulty providing sufficiently tight tolerance for a medical instrument employing a multi-gear mechanism. Injection molding, for example, may be desirable for mass production of low cost gears, but injection molding of a gear may have less control of tolerance than does machining of a gear.

In one implementation, roll mechanism 400 employs single piece plastic gears that can be produced inexpensively by injection molding. To minimize backlash, one or more of gears 410, 420, 430, 440, and 450 may be fit tightly in mechanism 400 for low backlash and may be compressible to compress to avoid interference even when the precision or tolerance in the manufacture of the gear train suggests that rigid gears would interfere with each other for some range of the manufacturing tolerance. FIG. 4A shows an example in which idler gear 420 has a compressible structure, but alternatively other gears in roll mechanism 400 may be compressible.

Figure 6A:
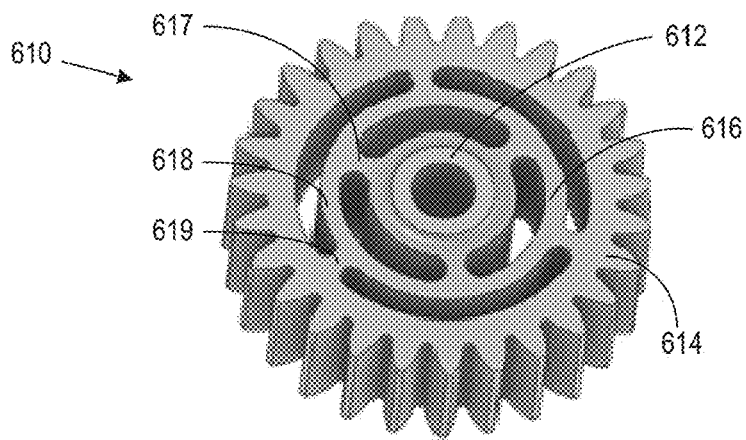
FIGS. 6A, 6B, 6C, and 6D illustrate some alternative implementations of compressible gears that may be employed in a roll mechanism.

FIG. 6A shows one example of a compressible gear 610, which includes a center inner ring piece 612, an outer ring 614, and a flexible interconnecting member 616 (sometimes called a "flexible webbing") all formed in a single structure that may be injection molded. Inner ring 612 acts as a hub of gear 610 and may fit onto a shaft or may include a shaft for gear 610. Outer ring 614 may be sized and have teeth shaped to mesh with adjacent gears in a gear train. Outer ring 614 may particularly have a nominal size such that the clearance with adjacent gears in a gear train is insufficient to accommodate variations in manufacturing and assembly, so that if outer ring 614 were rigid, interference may be expected to occur at some rotation angles in at least some assemblies of the gear train including gear 610. The tight clearance may be chosen to provide a backlash small enough for use in a medical instrument, even when the method for manufacture and assembly of the gear train is insufficient to otherwise guarantee the desired backlash. Outer ring 614 is supported by flexible member 616, which connects outer ring 614 to inner ring 612 and provides outer ring 614 with radial compliance. In particular, in an assembly in which the size, spacing, and run-out of gear 610 and adjacent gears could otherwise cause interference, outer ring 614 may flex in a radial direction enough to avoid interference.

Figure 6B:
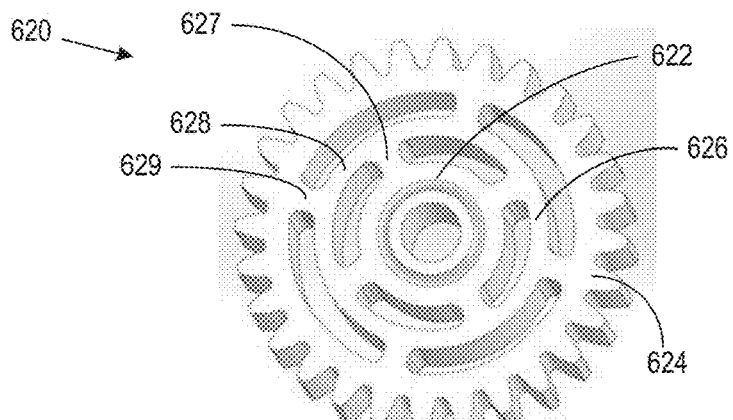

The illustrated specific implementation of flexible interconnecting member 616 illustrated in FIG. 6A includes a set of inner spokes 617 extending from inner ring 612 to a middle ring 618 and a set of outer spokes 619 extending from middle ring 618 to outer ring 614. Outer spokes 619 are not aligned with inner spokes 617, so that outer spokes 619 transfer pressure on outer ring 614 to a flexible span of middle ring 618. Since inner spokes 617 are separated from the points at which outer spoke 619 apply pressure to middle ring 618, portions of middle ring 618 and outer ring 612 can flex toward the shaft of gear 610. A gear 620 shown in FIG. 6B similarly uses a flexible interconnecting member 626 including inner spokes 627, a middle ring 628, and outer spokes 629 to connect an inner ring or hub 622 to a toothed output ring 624. The implementations of gears 610 and 620 differ in the number of inner and outer spokes. Gear 610 has three inner spokes 617 and three outer spokes 619, and gear 620 has four inner spokes 627 and four outer spokes 629. More generally, the number of inner and outer spokes and the dimensions and material used in the outer and middle rings can be varied to vary the flexibility of a gear implementation that employs offset spokes. And, various designs of flexible webbing or similar structural support between the inner piece and the outer ring may be used.

Figure 6C:
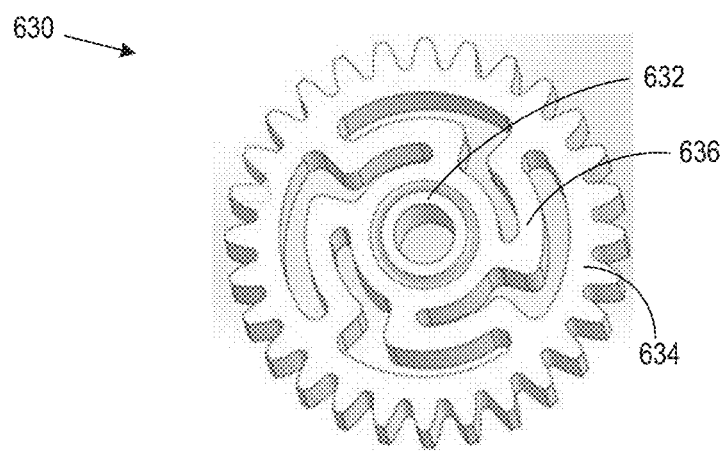

For example, FIG. 6C illustrates a flexible gear 630 in accordance with an implementation in which a flexible interconnecting member 636 includes a set of curved spokes that connect an inner hub ring 632 to a toothed outer ring 634. Each of the curved spokes may include an inner portion connected to inner ring 632, an outer portion connected to outer ring 634, and a cantilever connecting the inner and outer portions of the spoke. When pressure is applied to outer ring 634, force may be transferred through the outer portion of a spoke to the cantilever, which may flex in response to the force and allow a portion of outer ring 634 to inwardly deflect.

Figure 6D:
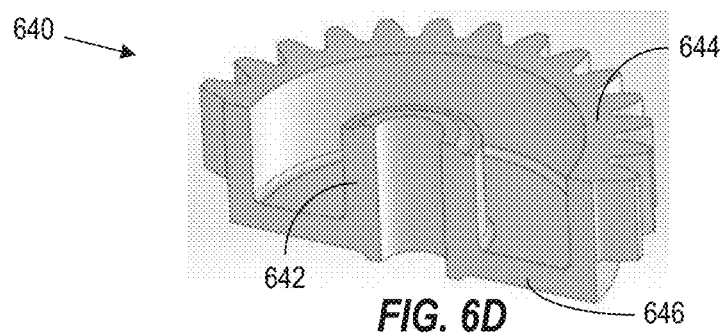

As another example, FIG. 6D illustrates a flexible gear 640 in accordance with an implementation in which an interconnecting member 646 connects an inner hub ring 642 to an outer toothed ring 644 only along one edge (e.g., a bottom edge) of inner ring 642 and outer ring 644. As a result, only one edge of outer ring 644 is radially supported, and an unsupported edge of outer ring 644 can inwardly flex. Considered as a whole, therefore, the outer ring 644 can flex radially inward.

FIGS. 6A to 6D illustrate some example implementations of compressible gears that may be molded as a single piece, e.g., by injection molding of a plastic material. Many other implementations of molded gears are possible. Alternatively, a compressible gear may be made of multiple materials, e.g., by connecting inner and outer rings made of a resilient material with an interconnecting material that is more compliant or compressible.

The amount of backlash that is acceptable in a medical instrument may be related to the allowable position error of the tip of the instrument. For example, if the length between joints 211 and 212 in instrument 110 of FIG. 2A is 50 mm, and joint 211 can move ±45°, then the tip of the instrument may roll at a maximum 35 mm radius around the shaft 114. If the position of the tip may vary by 1 mm without being detrimental to the surgeon, then the allowable total backlash and compliance in the roll mechanism is 1/35=0.028 radians=1.6°. These numbers are merely examples, but such permitted backlash for an instrument may be budgeted to the assembly of all the components in the roll mechanism, including but not limited to, the rotational clearances in the shaft components, the twisting compliance of the shaft, and the clearance in the gear mesh.

A process for designing a gear train such as used in roll mechanism 400 of FIG. 4 can take into account the ability of one or more gears to compress. For example, a maximum permissible amount of backlash in a gear train for a medical instrument may dictate a tight mesh, e.g., a minimum size of the gear teeth and maximum spacing from center to center of gears. Considering both the manufacturing tolerances of the gear housing or chassis and the run-out of each gear in the gear train, the tight mesh could be an interference fit. In particular, if a manufactured gear has some run-out or variation in tooth width, the gear may transition from clearance at one angle to interference at another. However, the flexibility of the outer ring and the flexible connection to the inner ring in a compressible gear may allow the teeth to deflect radially inward, away from the interference, so that the gear continues to run smoothly across the teeth of the mating gear. Backlash is thus minimized, but the gears do not jam and may be manufactured with reasonable tolerances.

Although particular implementations have been disclosed, these implementations are only examples and should not be taken as limitations. Aspects have been described in the context of a shaft roll mechanism, but these aspects apply to other implementations in medical instrument or medical robotic systems. And, although aspects have been described within a medical context or for a medical procedure, the techniques described herein can also be used within non-medical contexts and non-medical procedures.

Various adaptations and combinations of features of the implementations disclosed are within the scope of the following claims.

What is claimed is:

1. A medical instrument, comprising:
an instrument shaft defining a first rotation axis;
an input shaft defining a second rotation axis, the first rotation axis being offset from the second rotation axis by an acute angle;
a beveloid gear positioned to transfer a rotation of the input shaft about the second rotation axis to the instrument shaft to rotate the instrument shaft about the first rotation axis; and
a spur gear mounted to a common shaft with the beveloid gear, the spur gear being positioned to receive the rotation of the input shaft.

2. The medical instrument of claim 1, wherein:
the beveloid gear and the spur gear are formed as a single monolithic structure.

3. The medical instrument of claim 1, further comprising:
an output gear coupled to the instrument shaft, the output gear being configured to mesh with the beveloid gear and receive a rotational input from the beveloid gear.

4. The medical instrument of claim 3, further comprising:
a mounting sized to receive the instrument shaft, the output gear being fixedly coupled to the mounting.

5. The medical instrument of claim 4, wherein:
the mounting includes at least one bearing configured to support the instrument shaft.

6. The medical instrument of claim 3, wherein:
the spur gear is a first spur gear; and
the output gear is a second spur gear.

7. The medical instrument of claim 1, wherein:
the beveloid gear is coupled to the instrument shaft.

8. The medical instrument of claim 1, wherein:
the first rotation axis and the second rotation axis are coplanar.

9. The medical instrument of claim 1, wherein:
the beveloid gear includes a plurality of teeth;
each of the plurality of teeth have a helix angle; and
the first rotation axis and the second rotation axis define a skew therebetween determined at least in part by the helix angle.

10. A roll mechanism for a medical instrument, comprising:
a first gear defining a first rotation axis;
a second gear defining a second rotation axis, the second rotation axis defining a non-zero angle with the first rotation axis;
a third gear coupled to a common shaft; and
a beveloid gear coupled to the common shaft, the beveloid gear being rotatable with the third gear on the common shaft, the beveloid gear being positioned transfer a rotational motion from the second gear to the first gear to rotate the first gear about the first rotation axis.

11. The roll mechanism for a medical instrument of claim 10, wherein:
the second rotation axis defines an acute angle with the first rotation axis.

12. The roll mechanism for a medical instrument of claim 10, wherein:
the first rotation axis and the second rotation axis are coplanar.

13. The roll mechanism for a medical instrument of claim 10, wherein:
the beveloid gear includes a plurality of teeth;
each of the plurality of teeth have a helix angle; and
the first rotation axis and the second rotation axis define a skew therebetween determined at least in part by the helix angle.

14. The roll mechanism for a medical instrument of claim 10, wherein:
the third gear and the beveloid gear are formed as a single monolithic structure.

15. The roll mechanism for a medical instrument of claim 10, wherein:
the beveloid gear includes a plurality of teeth; and
the teeth of the plurality of teeth are arranged with a helical tooth pattern.

16. The roll mechanism for a medical instrument of claim 10, further comprising:
an input spindle shaped to engage an actuator, the input spindle being rotatable about the second rotation axis.

17. The roll mechanism for a medical instrument of claim 10, wherein:
the common shaft is parallel to the second rotation axis.

18. The roll mechanism for a medical instrument of claim 10, further comprising:
an idler gear positioned between the second gear and the third gear, wherein:
the idler gear is meshed with the third gear,
the idler gear is compressible, and
the idler gear is rotatable about a shaft that is oriented parallel to the second rotation axis.

19. The roll mechanism for a medical instrument of claim 18, wherein:
the second rotation axis, the shaft, and the common shaft are parallel and coplanar.

* * * * *